(12) United States Patent
Sambandam

(10) Patent No.: US 12,023,031 B2
(45) Date of Patent: Jul. 2, 2024

(54) ANASTOMOSIS DEVICES

(71) Applicant: W. L. Gore & Associates, Inc., Newark, DE (US)

(72) Inventor: Sakthi Sambandam, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 373 days.

(21) Appl. No.: 16/520,651

(22) Filed: Jul. 24, 2019

(65) Prior Publication Data

US 2020/0015823 A1 Jan. 16, 2020

Related U.S. Application Data

(63) Continuation of application No. 14/701,338, filed on Apr. 30, 2015, now Pat. No. 10,363,040.
(Continued)

(51) Int. Cl.
*A61B 17/11* (2006.01)
*A61B 17/00* (2006.01)
(Continued)

(52) U.S. Cl.
CPC ...... *A61B 17/1114* (2013.01); *A61B 17/0057* (2013.01); *A61B 17/11* (2013.01); *A61F 2/06* (2013.01); *A61F 2/90* (2013.01); *A61B 17/064* (2013.01); *A61B 2017/0641* (2013.01); *A61B 17/08* (2013.01); *A61B 17/083* (2013.01);
(Continued)

(58) Field of Classification Search
CPC . A61B 17/0057; A61B 17/11; A61B 17/1114; A61B 17/1128; A61B 17/1146; A61B 2017/00575; A61B 2017/00597; A61B 2017/00606; A61B 2017/00637; A61B 2017/00641; A61B 2017/00646; A61B 2017/00676; A61B 2017/1107; A61B 2017/1117; A61B 2017/1132;
(Continued)

(56) References Cited

U.S. PATENT DOCUMENTS 3,818,511 A  6/1974 Goldberg et al.
4,119,100 A  10/1978 Rickett
(Continued)

FOREIGN PATENT DOCUMENTS

CN  101374477 A  2/2009
CN  201379668 Y  1/2010
(Continued)

OTHER PUBLICATIONS

International Preliminary Report on Patentability received for PCT Patent Application No. PCT/US15/28711, dated Nov. 17, 2016, 11 pages.
(Continued)

*Primary Examiner* — Todd J Scherbel

(57) ABSTRACT

Implantable medical devices for connecting tissue layers, such as for connecting a gallbladder and a portion of a gastrointestinal tract to create an anastomosis, include a tubular structure having a plurality of apposition portions, a central region, and a covering material. The devices are endoscopically deployable and may include flange members having hinge members or variable properties such as length, angle, shape, material stiffness, and wire diameter.

18 Claims, 6 Drawing Sheets

Related U.S. Application Data

(60) Provisional application No. 61/987,954, filed on May 2, 2014.

(51) Int. Cl.
*A61F 2/06* (2013.01)
*A61F 2/90* (2013.01)
*A61B 17/064* (2006.01)
*A61B 17/08* (2006.01)
*A61F 2/07* (2013.01)

(52) U.S. Cl.
CPC ............ *A61B 2017/1103* (2013.01); *A61B 2017/1107* (2013.01); *A61B 2017/1132* (2013.01); *A61B 2017/1135* (2013.01); *A61B 2017/1139* (2013.01); *A61F 2002/077* (2013.01)

(58) Field of Classification Search
CPC .... A61B 2017/1135; A61B 2017/1139; A61B 2017/1142
See application file for complete search history.

(56) References Cited

U.S. PATENT DOCUMENTS

| | | | |
|---|---|---|---|
| 4,338,937 A | 7/1982 | Lerman | |
| 4,381,765 A | 5/1983 | Burton | |
| 5,171,259 A | 12/1992 | Inoue | |
| 5,224,953 A | 7/1993 | Morgentaler | |
| 5,261,898 A | 11/1993 | Polin et al. | |
| 5,354,308 A | 10/1994 | Simon et al. | |
| 5,562,728 A | 10/1996 | Lazarus et al. | |
| 5,741,297 A | 4/1998 | Simon | |
| 5,755,778 A | 5/1998 | Kleshinski | |
| 5,797,933 A | 8/1998 | Snow et al. | |
| 5,824,041 A | 10/1998 | Lenker et al. | |
| 5,830,222 A | 11/1998 | Makower | |
| 5,868,783 A | 2/1999 | Tower | |
| 5,945,994 A | 8/1999 | Shimizu et al. | |
| 5,957,949 A | 9/1999 | Leonhardt et al. | |
| 6,007,544 A | 12/1999 | Kim | |
| 6,077,291 A | 6/2000 | Das | |
| 6,120,534 A | 9/2000 | Ruiz | |
| 6,165,209 A | 12/2000 | Patterson et al. | |
| 6,168,617 B1 | 1/2001 | Blaeser et al. | |
| 6,168,621 B1 | 1/2001 | Vrba | |
| 6,171,329 B1 | 1/2001 | Shaw et al. | |
| 6,193,734 B1 | 2/2001 | Bolduc et al. | |
| 6,214,029 B1 | 4/2001 | Thill et al. | |
| 6,217,608 B1 | 4/2001 | Penn et al. | |
| 6,290,728 B1 | 9/2001 | Phelps et al. | |
| 6,315,708 B1 | 11/2001 | Salmon et al. | |
| 6,315,792 B1 | 11/2001 | Armstrong et al. | |
| 6,355,052 B1 | 3/2002 | Neuss et al. | |
| 6,391,036 B1 | 5/2002 | Berg et al. | |
| 6,391,039 B1 | 5/2002 | Nicholas et al. | |
| 6,416,543 B1 | 7/2002 | Hilaire et al. | |
| 6,419,681 B1 | 7/2002 | Vargas et al. | |
| 6,432,127 B1 | 8/2002 | Kim et al. | |
| 6,468,303 B1 | 10/2002 | Amplatz et al. | |
| 6,485,496 B1 | 11/2002 | Suyker et al. | |
| 6,485,507 B1 | 11/2002 | Walak et al. | |
| 6,488,702 B1 | 12/2002 | Besselink | |
| 6,579,314 B1 | 6/2003 | Lombardi et al. | |
| 6,585,758 B1 | 7/2003 | Chouinard et al. | |
| 6,616,675 B1 | 9/2003 | Evard | |
| 6,629,992 B2 | 10/2003 | Bigus et al. | |
| 6,666,883 B1 | 12/2003 | Seguin et al. | |
| 6,712,836 B1 | 3/2004 | Berg et al. | |
| 6,830,575 B2 | 12/2004 | Stenzel et al. | |
| 6,863,684 B2 | 3/2005 | Kim et al. | |
| 6,866,674 B2 | 3/2005 | Galdonik et al. | |
| 6,911,037 B2 | 6/2005 | Gainor et al. | |
| 6,945,994 B2 | 9/2005 | Austin et al. | |
| 6,958,037 B2 | 10/2005 | Ewers et al. | |
| 7,022,131 B1 | 4/2006 | Derowe et al. | |
| 7,025,777 B2 | 4/2006 | Moore | |
| 7,029,482 B1 | 4/2006 | Vargas et al. | |
| 7,037,344 B2 | 5/2006 | Kagan et al. | |
| 7,115,136 B2 | 10/2006 | Park et al. | |
| 7,182,771 B1 | 2/2007 | Houser et al. | |
| 7,223,274 B2 | 5/2007 | Vargas et al. | |
| 7,252,680 B2 | 8/2007 | Freitag | |
| 7,303,569 B2 | 12/2007 | Yencho et al. | |
| 7,431,729 B2 | 10/2008 | Chanduszko | |
| 7,527,644 B2 | 5/2009 | Mangiardi et al. | |
| 7,547,321 B2 | 6/2009 | Silvestri et al. | |
| 7,585,306 B2 | 9/2009 | Abbott et al. | |
| 7,608,086 B2 | 10/2009 | Tanaka et al. | |
| 7,632,302 B2 | 12/2009 | Vreeman et al. | |
| 7,780,686 B2 | 8/2010 | Park et al. | |
| 7,828,814 B2 | 11/2010 | Brenneman et al. | |
| 7,892,247 B2 | 2/2011 | Conston et al. | |
| 7,901,430 B2 | 3/2011 | Matsuura et al. | |
| 8,029,534 B2 | 10/2011 | Hruska et al. | |
| 8,043,360 B2 * | 10/2011 | McNamara | A61F 2/2442 623/1.15 |
| 8,109,946 B2 | 2/2012 | Cahill et al. | |
| 8,114,125 B2 | 2/2012 | Seibold et al. | |
| 8,197,498 B2 | 6/2012 | Coleman et al. | |
| 8,257,389 B2 | 9/2012 | Chanduszko et al. | |
| 8,262,691 B2 | 9/2012 | McGuckin et al. | |
| 8,343,088 B2 | 1/2013 | Bates et al. | |
| 8,398,676 B2 | 3/2013 | Roorda et al. | |
| 8,409,167 B2 | 4/2013 | Roschak | |
| 8,425,539 B2 | 4/2013 | Binmoeller et al. | |
| 8,430,934 B2 | 4/2013 | Das | |
| 8,435,284 B2 | 5/2013 | Eidenschink et al. | |
| 8,454,632 B2 | 6/2013 | Binmoeller et al. | |
| 8,579,935 B2 | 11/2013 | Devries et al. | |
| 8,641,747 B2 | 2/2014 | Brenneman et al. | |
| 8,679,171 B2 | 3/2014 | Deem et al. | |
| 8,728,155 B2 | 5/2014 | Montorfano et al. | |
| 8,740,940 B2 | 6/2014 | Maahs et al. | |
| 8,864,813 B2 | 10/2014 | Barr | |
| 8,870,916 B2 | 10/2014 | Ewers et al. | |
| 8,992,604 B2 | 3/2015 | Gross et al. | |
| 9,597,204 B2 | 3/2017 | Benary et al. | |
| 9,668,853 B2 | 6/2017 | Shin | |
| 9,782,533 B2 | 10/2017 | Brenneman et al. | |
| 9,993,251 B2 | 6/2018 | Todd et al. | |
| 10,004,509 B2 | 6/2018 | Todd | |
| 10,363,040 B2 | 7/2019 | Sambandam | |
| 10,806,458 B2 | 10/2020 | Todd | |
| 11,439,396 B2 | 9/2022 | Johnson et al. | |
| 11,712,230 B2 | 8/2023 | Johnson et al. | |
| 11,724,075 B2 | 8/2023 | Johnson | |
| 2001/0021872 A1 * | 9/2001 | Bailey | A61F 2/07 623/1.24 |
| 2001/0047180 A1 | 11/2001 | Grudem et al. | |
| 2002/0082627 A1 | 6/2002 | Berg et al. | |
| 2002/0099431 A1 | 7/2002 | Armstrong et al. | |
| 2002/0099437 A1 | 7/2002 | Anson et al. | |
| 2002/0161341 A1 | 10/2002 | Stinson et al. | |
| 2002/0169475 A1 | 11/2002 | Gainor et al. | |
| 2002/0183787 A1 | 12/2002 | Wahr et al. | |
| 2003/0028213 A1 | 2/2003 | Thill et al. | |
| 2003/0032967 A1 | 2/2003 | Park et al. | |
| 2003/0055441 A1 | 3/2003 | Suyker et al. | |
| 2003/0069533 A1 | 4/2003 | Kakutani et al. | |
| 2003/0093096 A1 | 5/2003 | McGuckin et al. | |
| 2003/0109893 A1 | 6/2003 | Vargas et al. | |
| 2003/0120292 A1 | 6/2003 | Park et al. | |
| 2003/0139819 A1 | 7/2003 | Beer et al. | |
| 2003/0144578 A1 | 7/2003 | Kenneth | |
| 2003/0191482 A1 | 10/2003 | Suyker et al. | |
| 2003/0225421 A1 | 12/2003 | Peavey et al. | |
| 2004/0073242 A1 | 4/2004 | Chanduszko | |
| 2004/0078053 A1 | 4/2004 | Berg et al. | |
| 2004/0092977 A1 | 5/2004 | Vargas et al. | |
| 2004/0098105 A1 | 5/2004 | Stinson et al. | |
| 2004/0133236 A1 | 7/2004 | Chanduszko | |
| 2004/0204755 A1 | 10/2004 | Robin | |

(56) References Cited

U.S. PATENT DOCUMENTS

| | | |
|---|---|---|
| 2004/0211433 A1 | 10/2004 | Albright |
| 2005/0049675 A1* | 3/2005 | Wallace ............... A61B 17/11 623/1.13 |
| 2005/0055082 A1 | 3/2005 | Ben Muvhar et al. |
| 2005/0070934 A1 | 3/2005 | Tanaka et al. |
| 2005/0070935 A1 | 3/2005 | Ortiz |
| 2005/0070957 A1 | 3/2005 | Das |
| 2005/0149071 A1 | 7/2005 | Abbott et al. |
| 2005/0154465 A1 | 7/2005 | Hodges et al. |
| 2005/0228413 A1 | 10/2005 | Binmoeller et al. |
| 2005/0234509 A1 | 10/2005 | Widomski et al. |
| 2005/0251201 A1 | 11/2005 | Roue et al. |
| 2005/0273124 A1 | 12/2005 | Chanduszko |
| 2005/0288786 A1 | 12/2005 | Chanduszko |
| 2006/0047337 A1 | 3/2006 | Brenneman |
| 2006/0052821 A1 | 3/2006 | Abbott et al. |
| 2006/0106418 A1 | 5/2006 | Seibold et al. |
| 2006/0200228 A1 | 9/2006 | Penn et al. |
| 2006/0212055 A1 | 9/2006 | Karabey et al. |
| 2006/0217761 A1 | 9/2006 | Opolski |
| 2007/0055358 A1 | 3/2007 | Krolik et al. |
| 2007/0073337 A1 | 3/2007 | Abbott et al. |
| 2007/0123917 A1 | 5/2007 | Ortiz et al. |
| 2007/0168014 A1 | 7/2007 | Jimenez et al. |
| 2007/0244518 A1 | 10/2007 | Callaghan |
| 2007/0249985 A1 | 10/2007 | Brenneman et al. |
| 2007/0282430 A1 | 12/2007 | Thommen et al. |
| 2007/0283552 A1 | 12/2007 | Gale et al. |
| 2008/0086168 A1 | 4/2008 | Cahill |
| 2008/0091235 A1 | 4/2008 | Sirota |
| 2008/0243151 A1 | 10/2008 | Binmoeller |
| 2008/0262518 A1 | 10/2008 | Freudenthal |
| 2009/0076541 A1 | 3/2009 | Chin et al. |
| 2009/0090366 A1 | 4/2009 | Cuevas et al. |
| 2009/0093873 A1 | 4/2009 | Navia |
| 2009/0118745 A1 | 5/2009 | Paul, Jr. |
| 2009/0143713 A1 | 6/2009 | Van et al. |
| 2009/0187240 A1 | 7/2009 | Clerc et al. |
| 2009/0228038 A1 | 9/2009 | Amin |
| 2009/0240316 A1 | 9/2009 | Bruszewski |
| 2009/0270971 A1 | 10/2009 | Xiao et al. |
| 2009/0281557 A1 | 11/2009 | Sander et al. |
| 2010/0010520 A1 | 1/2010 | Takahashi et al. |
| 2010/0023132 A1 | 1/2010 | Imran |
| 2010/0036401 A1 | 2/2010 | Navia |
| 2010/0100105 A1 | 4/2010 | Bates et al. |
| 2010/0106171 A1* | 4/2010 | Arepally ............... A61B 17/11 606/153 |
| 2010/0114128 A1 | 5/2010 | Coleman et al. |
| 2010/0114290 A1 | 5/2010 | Rasmussen et al. |
| 2010/0130995 A1 | 5/2010 | Yevzlin et al. |
| 2010/0174253 A1 | 7/2010 | Cline et al. |
| 2010/0234878 A1 | 9/2010 | Hruska et al. |
| 2010/0256548 A1* | 10/2010 | McNamara ............... A61F 2/06 604/9 |
| 2010/0268316 A1 | 10/2010 | Brenneman |
| 2010/0305590 A1 | 12/2010 | Holmes et al. |
| 2011/0040366 A1 | 2/2011 | Goetz et al. |
| 2011/0054381 A1 | 3/2011 | Van et al. |
| 2011/0060398 A1 | 3/2011 | Tupil et al. |
| 2011/0118765 A1 | 5/2011 | Aguirre |
| 2011/0125244 A1 | 5/2011 | Roeder et al. |
| 2011/0137410 A1* | 6/2011 | Hacohen ............... A61F 2/2409 623/2.37 |
| 2011/0213415 A1 | 9/2011 | McGuckin et al. |
| 2011/0218609 A1 | 9/2011 | Chobotov et al. |
| 2011/0257461 A1 | 10/2011 | Lipperman et al. |
| 2011/0257723 A1 | 10/2011 | McNamara |
| 2011/0301689 A1 | 12/2011 | Dorn et al. |
| 2012/0065652 A1 | 3/2012 | Cully |
| 2012/0089216 A1 | 4/2012 | Rapaport et al. |
| 2012/0130417 A1 | 5/2012 | Lepulu et al. |
| 2012/0172927 A1 | 7/2012 | Campbell et al. |
| 2012/0232505 A1 | 9/2012 | Eskaros et al. |
| 2012/0241503 A1 | 9/2012 | Baxter, III et al. |
| 2012/0283811 A1 | 11/2012 | Neilan |
| 2013/0012969 A1 | 1/2013 | Shin |
| 2013/0030351 A1 | 1/2013 | Belhe et al. |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0096606 A1 | 4/2013 | Bruchman et al. |
| 2013/0165967 A1 | 6/2013 | Amin et al. |
| 2013/0197623 A1 | 8/2013 | McHugo |
| 2013/0218192 A1 | 8/2013 | Erzberger et al. |
| 2013/0245742 A1 | 9/2013 | Norris |
| 2013/0261531 A1 | 10/2013 | Gallagher et al. |
| 2013/0317546 A1 | 11/2013 | Brown |
| 2014/0012368 A1 | 1/2014 | Sugimoto et al. |
| 2014/0074155 A1 | 3/2014 | Rothstein |
| 2014/0236064 A1 | 8/2014 | Binmoeller et al. |
| 2014/0303710 A1 | 10/2014 | Zhang et al. |
| 2014/0343602 A1 | 11/2014 | Cox et al. |
| 2015/0005810 A1 | 1/2015 | Center et al. |
| 2015/0066077 A1 | 3/2015 | Akpinar |
| 2015/0250630 A1 | 9/2015 | Irwin et al. |
| 2015/0265437 A1 | 9/2015 | Fleury et al. |
| 2015/0313595 A1 | 11/2015 | Houghton et al. |
| 2015/0313598 A1 | 11/2015 | Todd et al. |
| 2015/0313599 A1 | 11/2015 | Johnson et al. |
| 2016/0045199 A1* | 2/2016 | Mooney ............ A61B 17/00234 606/155 |
| 2016/0074023 A1 | 3/2016 | Sakamoto et al. |
| 2016/0135813 A1 | 5/2016 | Johnson et al. |
| 2016/0256169 A1 | 9/2016 | Ben-Muvhar et al. |
| 2017/0020498 A1 | 1/2017 | Blom |
| 2017/0105854 A1 | 4/2017 | Treacy et al. |
| 2018/0221194 A1 | 8/2018 | Eskaros et al. |
| 2018/0242972 A1 | 8/2018 | Todd |
| 2018/0250009 A1 | 9/2018 | Todd et al. |
| 2018/0296809 A1 | 10/2018 | Johnson |
| 2019/0298909 A1 | 10/2019 | Cully et al. |
| 2020/0146680 A1 | 5/2020 | Houghton et al. |
| 2021/0085328 A1 | 3/2021 | Todd |
| 2022/0257252 A1 | 8/2022 | Todd et al. |
| 2022/0370071 A1 | 11/2022 | Johnson et al. |
| 2023/0255632 A1 | 8/2023 | Todd |
| 2023/0320714 A1 | 10/2023 | Johnson et al. |
| 2023/0338714 A1 | 10/2023 | Johnson |

FOREIGN PATENT DOCUMENTS

| | | |
|---|---|---|
| CN | 101951983 A | 1/2011 |
| CN | 102083391 A | 6/2011 |
| CN | 102395323 A | 3/2012 |
| CN | 202801864 U | 3/2013 |
| CN | 103200975 A | 7/2013 |
| CN | 103209649 A | 7/2013 |
| CN | 103313681 A | 9/2013 |
| CN | 104244843 A | 12/2014 |
| CN | 106413586 A | 2/2017 |
| EP | 0991375 A1 | 4/2000 |
| EP | 1790297 A1 | 5/2007 |
| EP | 1480565 B1 | 12/2008 |
| EP | 2543323 A1 | 1/2013 |
| EP | 3136984 A1 | 3/2017 |
| GB | 2409978 A | 7/2005 |
| JP | 2000-505316 A | 5/2000 |
| JP | 2001-501493 A | 2/2001 |
| JP | 2001-520908 A | 11/2001 |
| JP | 2001-340346 A | 12/2001 |
| JP | 2003-527939 A | 9/2003 |
| JP | 2004-049806 A | 2/2004 |
| JP | 2005-503881 A | 2/2005 |
| JP | 2005-518863 A | 6/2005 |
| JP | 2005-528181 A | 9/2005 |
| JP | 2005-534390 A | 11/2005 |
| JP | 2006-006648 A | 1/2006 |
| JP | 2007-530128 A | 11/2007 |
| JP | 2009-508641 A | 3/2009 |
| JP | 2009-518149 A | 5/2009 |
| JP | 2010-523209 A | 7/2010 |
| JP | 2010-528821 A | 8/2010 |
| JP | 2011-509758 A | 3/2011 |

(56) References Cited

FOREIGN PATENT DOCUMENTS

| | | | |
|---|---|---|---|
| JP | 2011-519709 A | 7/2011 | |
| JP | 2013-013715 A | 1/2013 | |
| JP | 2014-503246 A | 2/2014 | |
| JP | 2015-500665 A | 1/2015 | |
| JP | 2021-155586 A | 10/2021 | |
| WO | 97/27898 A1 | 8/1997 | |
| WO | 97/32543 A1 | 9/1997 | |
| WO | 98/02099 A1 | 1/1998 | |
| WO | 98/08462 A2 | 3/1998 | |
| WO | 98/16174 A1 | 4/1998 | |
| WO | 98/58600 A1 | 12/1998 | |
| WO | 01/72367 A1 | 10/2001 | |
| WO | 2003/028522 A2 | 4/2003 | |
| WO | 03/73944 A1 | 9/2003 | |
| WO | 2003/103476 A2 | 12/2003 | |
| WO | 2004/012603 A2 | 2/2004 | |
| WO | 2004/087236 A2 | 10/2004 | |
| WO | 2005/089655 A1 | 9/2005 | |
| WO | 2006/121855 A2 | 11/2006 | |
| WO | 2007/024964 A1 | 3/2007 | |
| WO | 2007/053243 A2 | 5/2007 | |
| WO | WO-2007100970 | 9/2007 | |
| WO | 2008/157172 A1 | 12/2008 | |
| WO | 2009/091899 A2 | 7/2009 | |
| WO | 2009/109348 A1 | 9/2009 | |
| WO | 2009/140195 A1 | 11/2009 | |
| WO | 2009/146369 A1 | 12/2009 | |
| WO | 2010/129162 A1 | 11/2010 | |
| WO | WO-2012034108 A1 | 3/2012 | |
| WO | 2012/067912 A1 | 5/2012 | |
| WO | 2012/071075 A1 | 5/2012 | |
| WO | 2013/152891 A2 | 10/2013 | |
| WO | 2015/168501 A2 | 11/2015 | |
| WO | 2015/168504 A2 | 11/2015 | |
| WO | 2015/168506 A1 | 11/2015 | |
| WO | 2015/168507 A1 | 11/2015 | |
| WO | 2015/168508 A2 | 11/2015 | |

OTHER PUBLICATIONS

International Preliminary Report on Patentability received for PCT Patent Application No. PCT/US15/28715, dated Nov. 17, 2016, 8 pages.

International Preliminary Report on Patentability received for PCT Patent Application No. PCT/US15/28717, dated Nov. 17, 2016, 9 pages.

International Preliminary Report on Patentability received for PCT Patent Application No. PCT/US15/28721, dated Nov. 17, 2016, 8 pages.

International Search Report and Written Opinion from PCT/US2012/027984, dated Jun. 6, 2012, 11 pages.

International Search Report and Written Opinion from PCT/US2015/028707, dated Oct. 23, 2015, 19 pages.

International Search Report and Written Opinion from PCT/US2015/028721, dated Oct. 28, 2015, 13 pages.

International Search Report and Written Opinion from PCT/US2018/028120, dated Aug. 21, 2018, 17 pages.

International Search Report and Written Opinion received for PCT Patent Application No. PCT/US15/28711, dated Feb. 1, 2016, 17 pages.

International Search Report and Written Opinion received for PCT Patent Application No. PCT/US15/28715, dated Aug. 25, 2015, 12 pages.

International Search Report and Written Opinion received for PCT Patent Application No. PCT/US15/28717, dated Aug. 26, 2015, 13 pages.

International Search Report for PCT/US2016/055255 dated Dec. 20, 2016 and dated Jan. 20, 2017, 5 pages.

International Search Report, PCT/US2015/028715, dated Aug. 25, 2015, 5 pages.

* cited by examiner

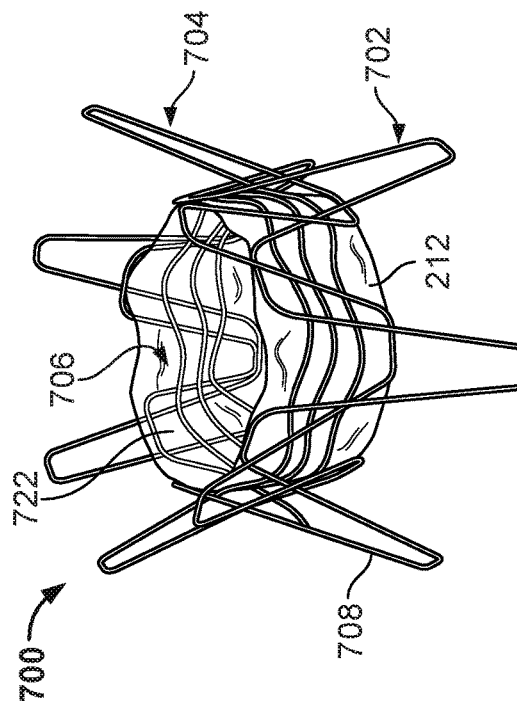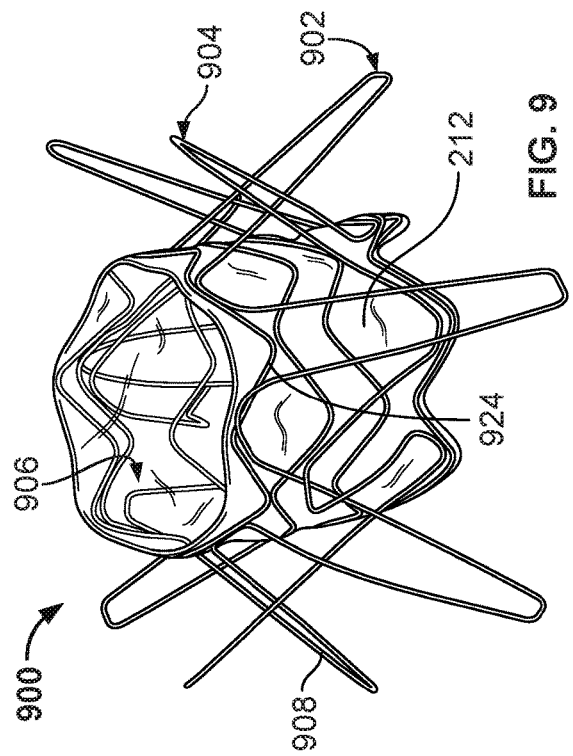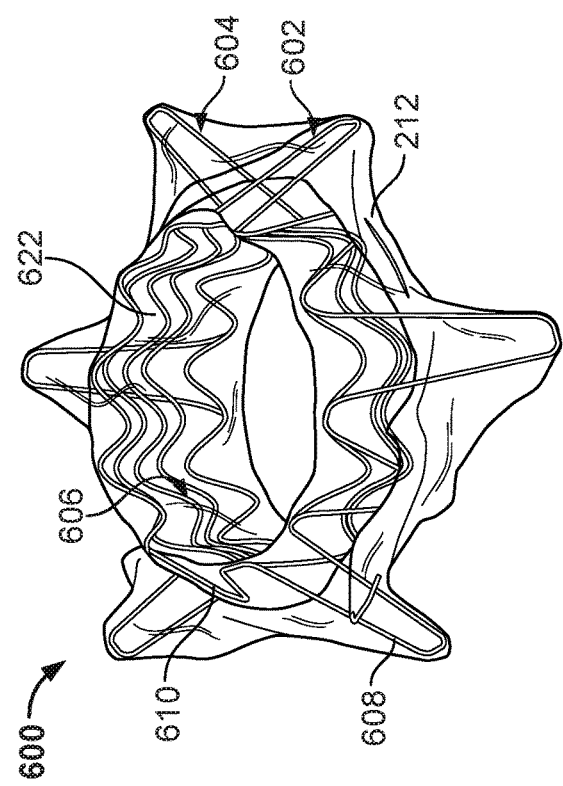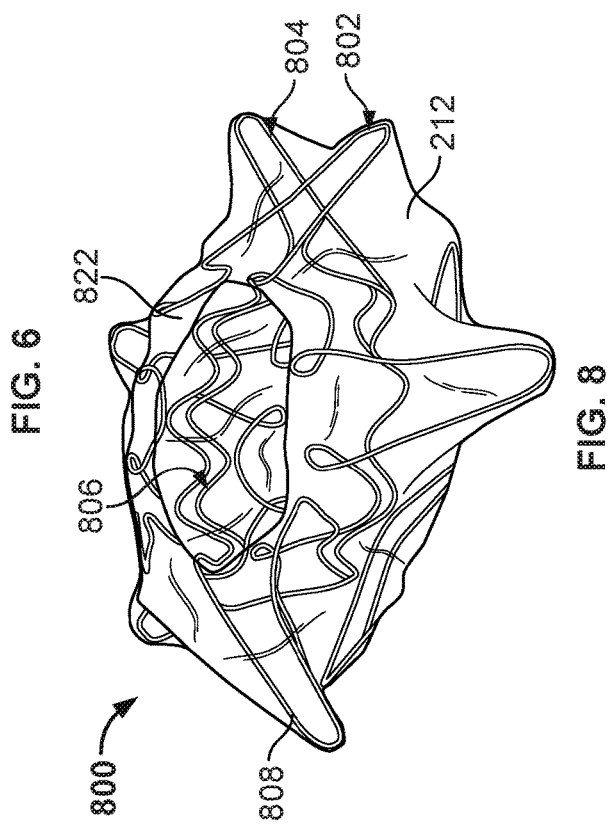

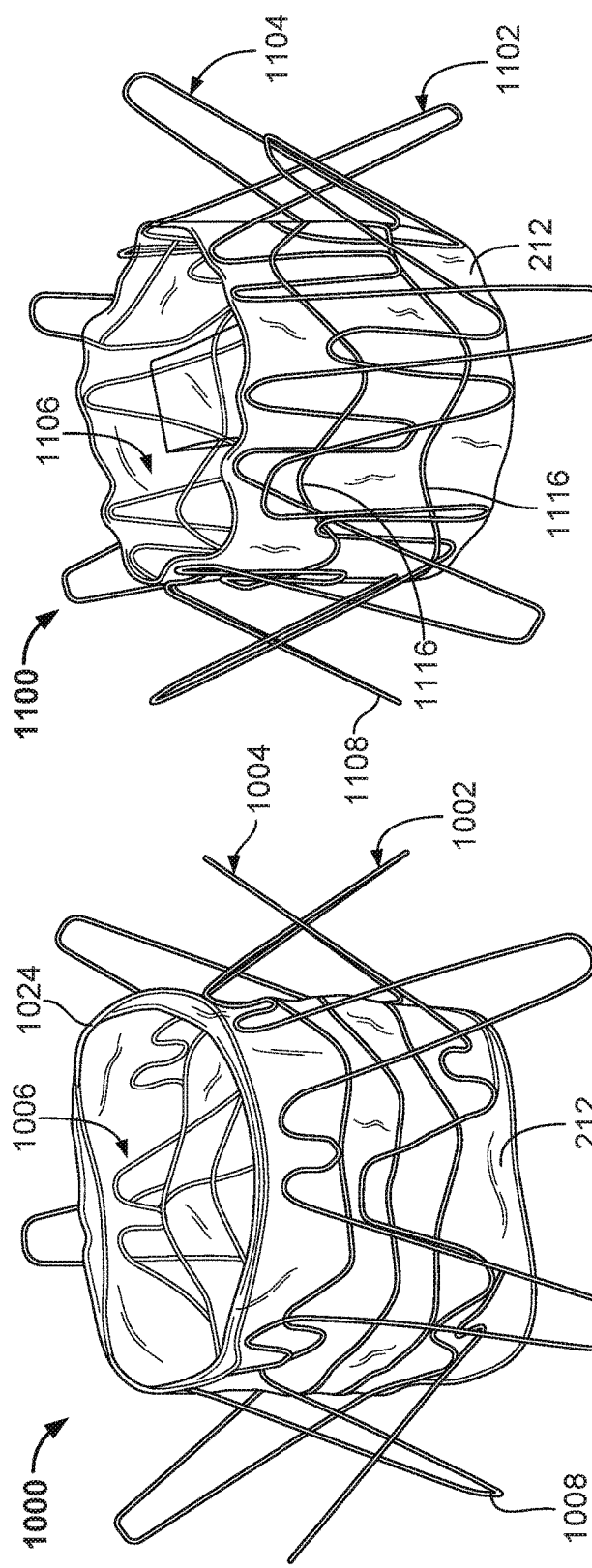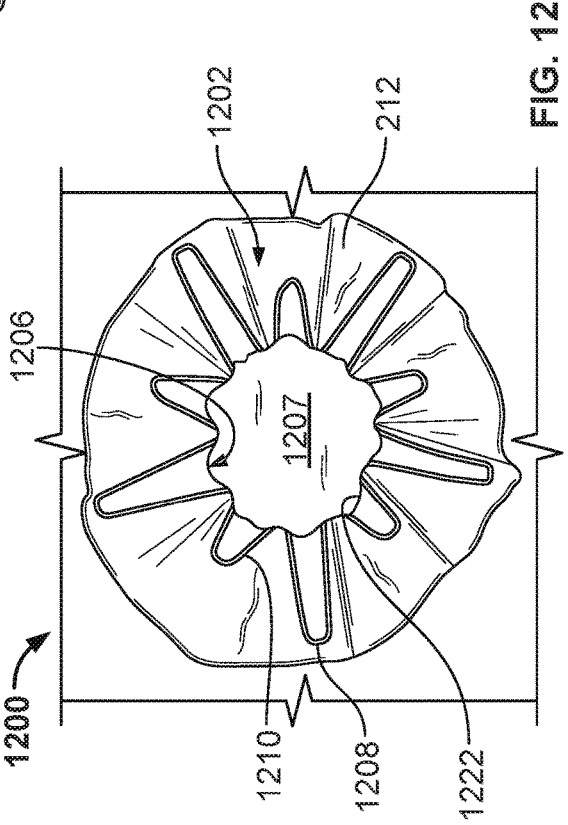

ANASTOMOSIS DEVICES

CROSS-REFERENCE TO RELATED APPLICATION

This application is a continuation of U.S. patent application Ser. No. 14/701,338, filed Apr. 30, 2015, which claims the benefit of U.S. Provisional Application 61/987,954, filed May 2, 2014, both of which are incorporated herein by reference in their entireties for all purposes.

FIELD

This present disclosure relates generally to implantable medical devices, and more specifically, to implantable devices for connecting tissue layers to create an anastomosis.

BACKGROUND

An anastomosis is a cross-connection between two tissue structures, such as blood vessels or intestines. For example, in the context of coronary artery bypass graft surgery, a graft vessel is anastomosed to a native coronary artery so that blood can flow through the graft vessel.

Anastomoses can be created in various manners including, but not limited to: end-to-end, end-to-side, and side-to-side anastomoses. Often, suturing is used to create such anastomoses.

SUMMARY

One aspect of the invention relates to an implantable medical device that includes (1) a barrel portion including a rigid frame having a first end and a second end, (2) a first flange portion including a plurality of first flange members having a first length and a plurality of second flange members having a second length where the first length is less than the second length, (3) a first hinge member including a cover material and flexibly coupling the first end of the barrel portion and the first flange portion, (4) a second flange portion including a plurality of the first flange members and a plurality of the second flange members, and (5) a second hinge member including the cover material. The second hinge member flexibly couples the second end of the barrel portion and the second flange portion. The first flange member may have a geometry and/or a stiffness that is different from that of the second flange member. In exemplary embodiments, the first flange member extends radially from the first and second hinge members at an angle less than 80 degrees and the second flange members extend radially from the first and second hinge members at an angle less than 90 degrees. In some embodiments, the first flange portion provides a first apposition force that is different from a second apposition force provided by the second flange portion. Additionally, at least a portion of the first flange portion and at least a portion of the second flange portion may be covered with a cover material.

A second aspect of the invention relates to an implantable medical device that includes (1) a barrel portion that includes a rigid frame having a first end and a second end, (2) a first flange portion that includes a plurality of first flange members having a first length and a plurality of second flange members having a second length, (3) a first hinge member that includes a cover material and flexibly couples the first end of the barrel portion and the first flange portion, (4) a second flange portion that includes a plurality of third flange members having a third length and a plurality of fourth flange members having a fourth length. The second hinge member includes the cover material and flexibly couples the second end of the barrel portion and the second flange portion. Additionally, in exemplary embodiments, the first length is less than the second length and the third length is less than the fourth length. Further, at least one of the first length and the second length is different from at least one of the third length and the fourth length. In some embodiments, the first flange members extend radially from the first and second hinge members at an angle less than 80 degrees and the second flange members extend radially from the first and second hinge members at an angle less than 90 degrees. In some embodiments, the first and second flange members include a first elongate member having a first geometry and the third and fourth flange members include a second elongate member having a second geometry that is different than the first geometry. In at least one embodiment, the first elongate member has a first stiffness and the second elongate member has a second stiffness that is different than the first stiffness. Additionally, in some embodiments, the first flange member provides a first apposition force, the second flange member provides a second apposition force, the third flange member provides a third apposition force, and the fourth flange member provides a fourth apposition force. Each of the first, second, third, and fourth apposition forces may be different.

A third aspect of the invention relates to an implantable medical device that includes (1) a barrel portion that includes a rigid frame having a first end and a second end, (2) a first flange portion that includes a plurality of first flange members having a first projecting angle and a plurality of second flange members having a second projecting angle that is different than the first projecting angle, (3) a first hinge member that includes a cover material and flexibly couples the first end of the barrel portion and the first flange portion, (4) a second flange portion that includes a plurality of first flange members having the first projecting angle and a plurality of second flange members having the second projecting angle, and (5) a second hinge member that includes the cover material and flexibly couples the second end of the barrel portion and the second flange portion. In at least one exemplary embodiment, the first projecting angle is between about 5 degrees and 80 degrees and the second projecting angle is between about 10 degrees and 90 degrees. The first flange member has a first length and the second flange member has a second length. In some embodiments, the first length is less than the second length. In some other embodiments, the first flange member includes a first elongate member having a first geometry and the second flange member includes a second elongate member having a second geometry that is different than the first geometry. Additionally, the first elongate member may have a stiffness that is different from the stiffness of the second elongate member. In at least one embodiment, the barrel portion includes an elongate member having a first stiffness and the first and second flange portions each include one or more elongate members having a second stiffness that is different than the first stiffness. In a further embodiment, the first flange portion provides a first apposition force and the second flange portion provides a second apposition force that is different than the first apposition force. Further, the first flange member provides a third apposition force and the second flange member provides a fourth apposition force that is different than the third apposition force.

DESCRIPTION OF DRAWINGS

The accompanying drawings are included to provide a further understanding of the disclosure and are incorporated in and constitute a part of this specification, illustrate embodiments, and together with the description serve to explain the principles of the disclosure.

FIG. 6 is a perspective view of another exemplary anastomosis device in accordance with some embodiments;

FIG. 7 is a perspective view of another exemplary anastomosis device in accordance with some embodiments;

FIG. 8 is a perspective view of another exemplary anastomosis device in accordance with some embodiments;

FIG. 9 is a perspective view of another exemplary anastomosis device in accordance with some embodiments;

FIG. 10 is a perspective view of another exemplary anastomosis device in accordance with some embodiments;

FIG. 11 is a perspective view of another exemplary anastomosis device in accordance with some embodiments;

FIG. 12 is a side view of another exemplary anastomosis device in accordance with some embodiments.

DETAILED DESCRIPTION

Figure 1:
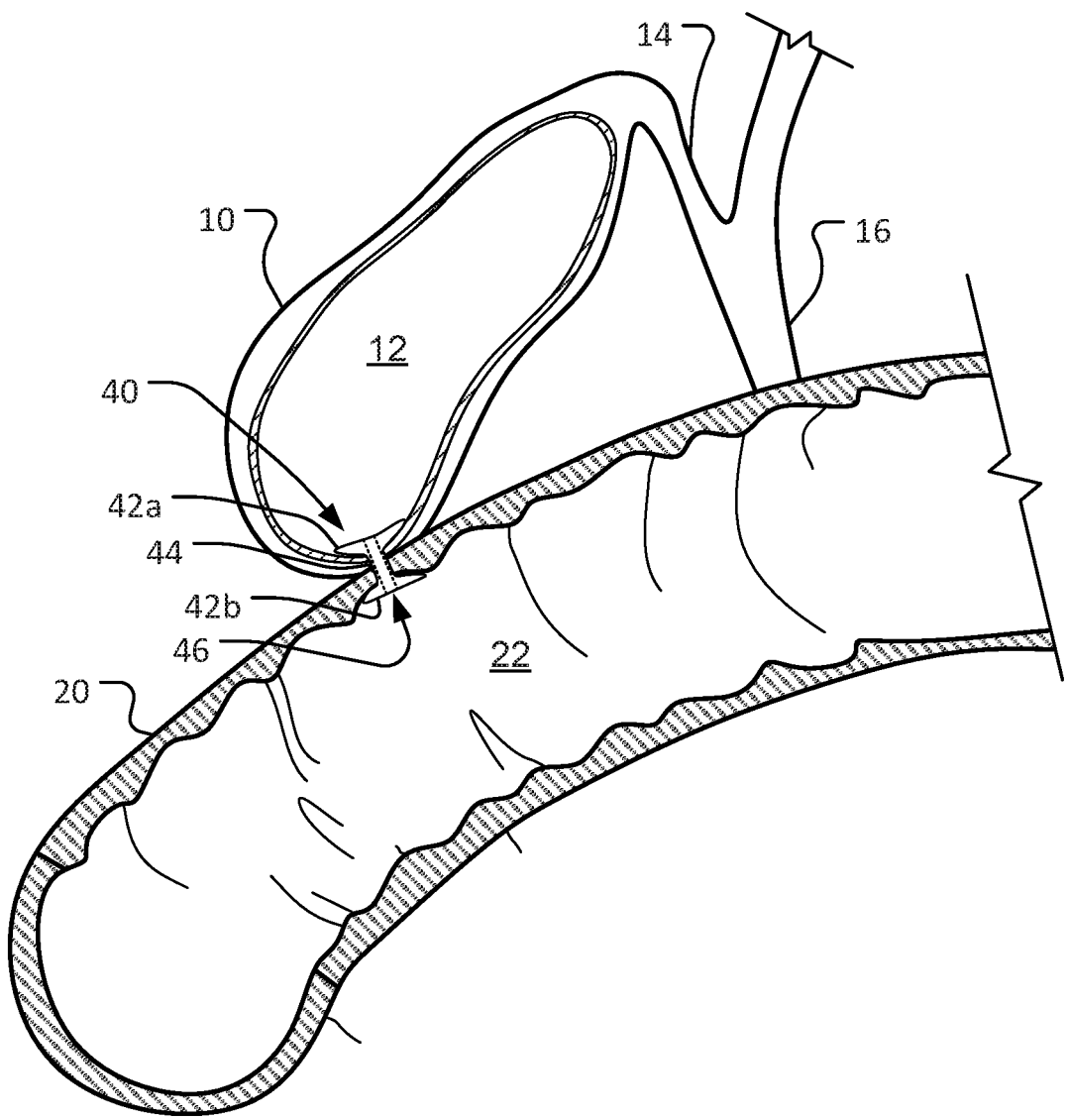
FIG. 1 is a cutaway perspective view of an exemplary anastomosis device that has been implanted within a patient to be a shunt between the patient's gallbladder and intestine in accordance with some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present invention is directed to implantable devices for connecting tissue layers, for example, to circumvent a conduit or organ blockage, such as by creating a direct passage between tissue structures (e.g. connecting a gallbladder and a portion of a gastrointestinal tract) to create an anastomosis that facilitates material flow therebetween. The devices described herein may be endoscopically deployable or deliverable via a catheter and may include self-expanding apposition mechanisms that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein are configured to be removable after implantation. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed. The devices described herein can provide alternative treatments for patients who are not suitable candidates for other types of treatments (e.g., gallbladder removal surgery) and/or to avoid known complications of other types of treatments (e.g., external biliary drainage).

The present disclosure refers to anastomosis devices in an exemplary fashion. That is, it should be understood that the inventive concepts disclosed in this document can also be applied to other types of devices. For example, this disclosure also provides implantable devices that, in some embodiments, can be used for occluding tissue structures, organs, body conduits, blood vessels, the GI tract, and the like. For example, in some embodiments the devices provided herein can be used to occlude septal defects. In some embodiments, the devices provided herein can be used to occlude a patient's vasculature or GI tract. In some such embodiments, the device does not include a tunnel through the device. Rather, in some embodiments a covering material seals the device to inhibit, modulate, or substantially prevent material from flowing through the device.

Referring to FIG. 1, an exemplary anastomosis device 40 in accordance with some embodiments provided herein can be implanted in a patient to create a fluidic connection between two organs, spaces, tissue structures, conduits, and the like, and combinations thereof. For example, in the depicted implementation the anastomosis device 40 is connecting a gall bladder 10 (that defines an internal gall bladder space 12) with an intestine 20 (that defines an internal intestinal space 22). Hence, the anastomosis device 40 is acting as a fluidic shunt device between the internal gall bladder space 12 and the internal intestinal space 22. Such an implementation may provide a beneficial treatment to the patient when, for example, a flow blockage exists in the native anatomical conduits connecting the internal gall bladder space 12 and the internal intestinal space 22. For example, in some instances the patient may have one or more gallstones that cause a blockage of the patient's cystic duct 14 and/or common bile duct 16. In such a case, the anastomosis device 40 can provide a fluidic passageway such that bile from the gall bladder 10 can flow into the intestine 20. If not for the anastomosis device 40, when bile is blocked from flowing out of the gall bladder 10 cholecystitis (inflammation of the gall bladder 10) may result.

While the anastomosis devices provided herein can be used in some implementations to relieve or prevent cholecystitis as described above, it should be understood that the anastomosis devices provided herein can also be used in many other types of implementations within a patient. For example, the anastomosis devices provided herein can be used in conjunction with various body tissue structures and organs such as, but not limited to, stomachs, colons, small intestines, pancreases, blood vessels, bladders, kidneys, conduits, and the like.

In general, some embodiments of the anastomosis devices provided herein (of which anastomosis device 40 is one example), include a first tissue flange portion 42a, a second tissue flange portion 42b, and a barrel portion 44 therebetween. The barrel portion 44 defines a lumen 46 that extends longitudinally from a first end of the anastomosis device 40 to a second end of the device 40. The lumen 46 acts as a connection (e.g., a shunt passageway) between the internal gall bladder space 12 and the internal intestinal space 22, such that the internal gall bladder space 12 is in fluid communication with the internal intestinal space 22 via the anastomosis device 40.

Figure 2:
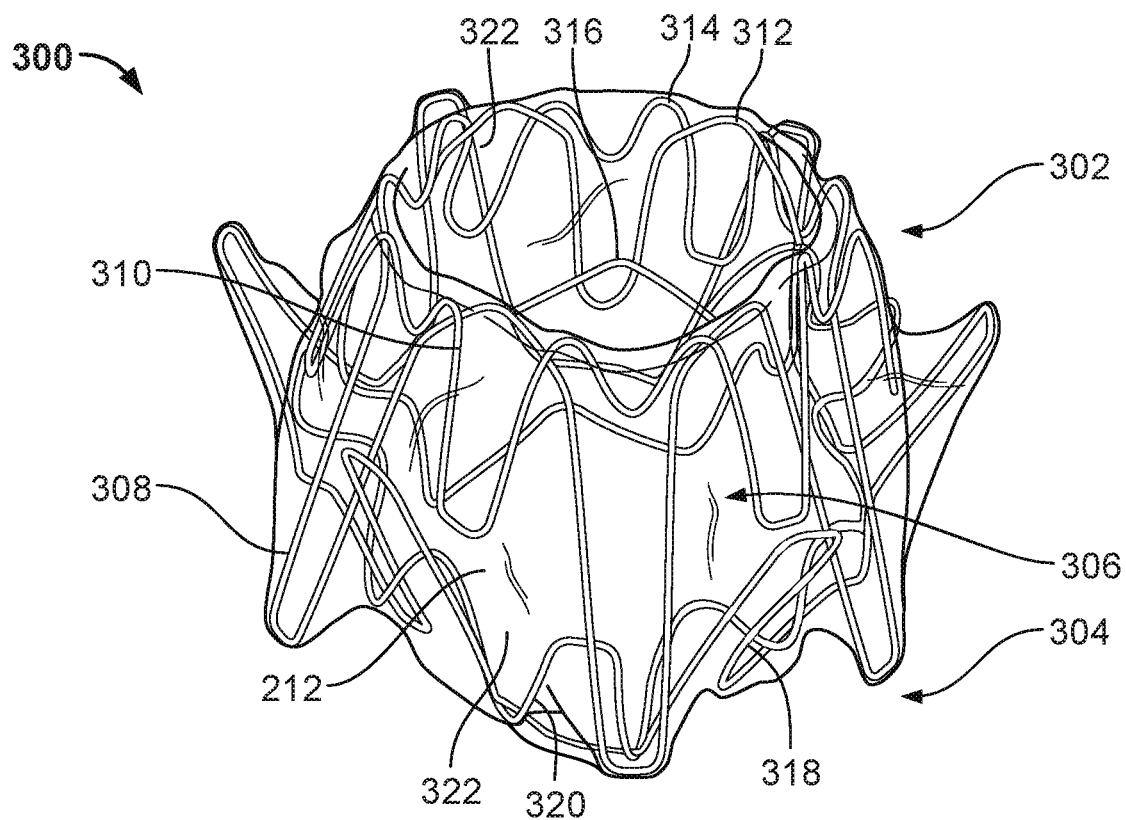
FIG. 2 is a perspective view of another exemplary anastomosis device in accordance with some embodiments.

Referring to FIG. 2, an anastomosis device 300 is shown having a barrel portion 306 or central portion that can be interchangeable with any barrel portion described here, a first flange portion 302, and a second flange portion 304. In some embodiments, the framework of device 300 or any portion thereof can comprise elongate elements such as a spring wire (e.g., L605 steel or stainless steels), shape memory alloy wire (e.g., nitinol or nitinol alloys), superelastic alloy wire (e.g., nitinol or nitinol alloys), other suitable types of wire, or combinations thereof. In the depicted embodiment of device 300, the framework is comprised of an elongate element that is formed by winding, for example. In some embodiments, different types of wires are used at different locations of the device 300. Alternatively, device 300 or portions thereof can be formed from the same piece of precursor material that is cut to create the elongate element framework structure as desired. In some embodiments, device 300 can be formed from a combination of one or more wound wires and one or more cut material portions. In some embodiments, the device 300 or portions thereof may be constructed of polymeric materials. The device 300 is shown with the covering material 212, as described herein.

The first flange portion 302 and the second flange portion 304 are configured to engage one or more layers of tissue therebetween, and to provide apposition forces against the tissue surfaces. The apposition forces provided by the first and second flange portions 302 and 304 can facilitate attachment of the device 300 to the tissue and provide displacement resistance such that the device 300 can reliably remain positioned at a target site in a patient as desired.

The first flange portion 302 and the second flange portion 304 (also referred to herein as apposition portions, flanges, etc.) can each include one or more flange members 308 and 310 (also referred to herein as anchor members, apposition members, fins, etc.). The flange members 308 and 310 can have a variety of different configurations (e.g., lengths, widths, shapes, angles, etc.). In some embodiments two or more flange members have the same configurations. In some embodiments, each of the flange members has the same configuration.

The anastomosis device 300 can be configured in a collapsed low-profile delivery configuration in which the framework is diametrically compressed and longitudinally extended such that the flange members 308 and 310 extend substantially parallel to the longitudinal axis of the device 300. In the deployed or expanded configuration, the flange members 308 and 310 extend from the barrel portion 306. The device 300 may exhibit, for example, beneficial fatigue resistance and elastic properties. In some embodiments, the materials of the device 300 allow the anastomosis devices to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen.

In some embodiments, the length of the flange members 308 and 310 are different in relation to each other to provide both sufficient apposition forces at the base or hole where access is created and migration resistance forces. For example, flange member 308 shown is generally longer than flange member 310. This configuration facilitates a fast and sustainable apposition of tissue to form an anastomosis. In some embodiments, the flange members 308 and 310 of varying lengths are alternated, are staggered, or are nested along the circumferential axis. In some embodiments, the flange members 308 and 310 within each flange portion 302 and/or 304 are uniform in length.

In some embodiments, the lengths of the flange members 308 and 310 are selected based on the size of tissue structures into which the device 300 is to be implanted. For example, if a first body conduit generally includes a smaller geometry than the second body conduit, differing flange lengths can be advantageous. In this example, the flange portion entering the smaller body conduit includes the flanges having a shorter length, while the longer flanges remain in the larger body conduit. The shorter flange length provides an appropriate fit for the smaller body conduit thus ensuring sufficient contact necessary for an anastomosis device, while the longer flanges provide anti-migratory forces that help to retain the device in place. In some embodiments, the short and long flanges are staggered, nested, or separated based on the flange portion.

The anastomosis device 300 (and other embodiments that share design features of the anastomosis device 300) can exhibit the following advantages. Having dissimilar lengths of flange members 308 and 310 can provide apposition at various target locations or zones. Having one or more such specific apposition zones may minimize or eliminate leakage of fluid or other contents that pass through the device lumen. Discrete flange members 308 and 310 designs that move independently of each other leads to better tissue/fin conformability with tissue topography. Better conformability can minimize tissue injury especially when used in a diseased tissue bed. The flexible discrete design of the flange members 308 and 310 can facilitate device 300 removal by folding the flange members 308 and 310 parallel to the lumen of the device 300. This flexibility of the flange members 308 and 310 design can reduce or minimize tissue injury during device removal. Multiple flange members 308 and 310 and short non-overlapping sinusoidal struts on the barrel portion 306 make the device 300 conformable. This conformability helps in easy tracking of the catheter through an endoscope working channel. While providing longitudinal conformability, the short sinusoidal pattern provides adequate radial strength to prevent radial compression of the device 300 by external tissue forces.

The anastomosis device 300 can be formed of one or more elongate members, such as wires in some embodiments. In some embodiments, the anastomosis device 300 can include multiple separate elongate members. For example, the anastomosis device 300 is illustrated in FIG. 2 as including elongate members 312, 314, 316, 318, and 320. The elongate members 312 and 314 can form part of the first flange portion 302, with the elongate member 312 forming the flange members 308 of the first flange portion 302 and the elongate member 314 forming the flange member 310 of the first flange portion 302. The elongate member 316 can form part of a rigid frame of the barrel portion 306 or central portion. The elongate members 318 and 320 can form part of the second flange portion 304, with the elongate member 318 forming the flange members 308 of the second flange portion 304 and the elongate member 320 forming the flange member 310 of the second flange portion 304. Each of the elongate members 312, 314, 316, 318, and 320 can be separate elongate members, connected by the covering material 212. The flange members 308 and 310 can be attached to the covering material 212 to form hinge members 322, allowing the flange members 308 and 310 to pivot with respect to the barrel portion 306 and pivot with respect to the elongate member 316. As the flange members 308 and 310 bend, the hinge members 322 also bend, rotating the hinge members 322 to create a pivoting action of the flange members 308 and 310. Proximal ends of the elongate members 312, 314, 318, and 320 mount in the covering material 212 to form the hinge members 322 pivotably mounted in or on the covering material 212. In some embodiments, the anastomosis device 300 can be formed with no rigid wire extending from the barrel portion 306 through the hinge members 322 to the flange portions 302 and 304. In some embodiments, the hinge members 322 can be more flexible and less rigid than portions of the barrel portion 306 having one or more elongate members 316. In some embodiments, the hinge members 322 can be formed of the covering material 212 without wire material at all as part of the hinge members 322.

In some embodiments, the anastomosis device 300 can include five separate elongate members. For example, two elongate members can comprise the first flange portion 302, such as elongate members 312 and 314, two elongate members can comprise the second flange portion 304, such as elongate members 318 and 320, and one elongate member can comprise the barrel portion 306, such as elongate member 316. Using five separate elongate elements can allow for a relatively strong framework structure while also allowing for relative motion of the first and second flange portions 302 and 304 about the hinge members 322 as described herein.

In some embodiments, the anastomosis device 300 can include three separate elongate members. For example, one elongate member can comprise the first flange portion 302, such as elongate member 312, one elongate member can comprise the second flange portion 304, such as elongate member 318, and one elongate member can comprise the barrel portion 306. In some embodiments, the number of elongate members can be varied as suitable for the application.

In some embodiments, the anastomosis device 300 can include the elongate member 316 forming a rigid frame for the barrel portion 306. The first flange portion 302 can include a plurality of the flange members 310 having a first length and a plurality of the flange members 308 having a second length, the first length being less than the second length. A first hinge member 322 includes the covering material 212 and flexibly couples a first end of the barrel portion 306 and the first flange portion 302. The second flange portion 302 can include a plurality of the flange members 310 and a plurality of the flange members 308. A second hinge member 322 includes the covering material 212 and flexibly couples a second end of the barrel portion 306 and the second flange portion 304.

In some embodiments, forming the flange members 308 and 310 to have different lengths relative to each other can allow for the anastomosis device 300 to have its strength tailored for a particular application. In some embodiments, length of the flange members 308 and/or 310 can be increased to distribute force over a greater area and apply less localized force. In some embodiments, length of the flange members 308 and/or 310 can be shortened to distribute force over a smaller area and apply greater localized force. In some embodiments, length of the flange members 308 can be increased to distribute force over a greater area and apply less localized force while length of the flange members 310 can be shortened to distribute force over a smaller area and apply greater localized force.

In some embodiments, the anastomosis device 300 can be substantially symmetric about a centerline axis. In some embodiments, the anastomosis device 300 need not be symmetric, but rather, length of specific flange members 308 and/or 310 can be shortened and/or lengthened as appropriate for a given application to increase localized force at one location and decrease localized force at another location. This can be allow for anastomosis device 300 to be tailored for particular applications, such as an application with diseased tissue benefiting from a particular force distribution. In applications with diseased tissue, the anastomosis device 300 can be designed to apply reduced force in an area of that diseased tissue, such as by using elongated flange members 308. In some embodiments, the flange members 308 and 310 of the first flange portion 302 can provide force at a different location on a layer of tissue than a location of an apposed force applied by the flange members 308 and 310 of the second flange portion 304.

In some embodiments, other variables relating to the flange members 308 and 310 can be varied in addition to length in order to vary force distribution. For example, the wire diameter of one, some, or all of the flange members 308 and 310 can be increased or decreased. As an additional example, the projection angle of one, some, or all of the flange members 308 and 310 can be increased or decreased. As an additional example, the number of one, some, or all of the flange members 308 and 310 can be increased or decreased. As an additional example, the material stiffness of one, some, or all of the flange members 308 and 310 can be increased or decreased. One or more of these variables can be varied in one or more flange members 308 and 310 in addition to or instead of varying length so as to vary force distribution of the flange portions 302 and 304.

In some embodiments, the flange members 308 have a length of about 10 to 15 millimeters. In some embodiments, the flange members 310 have a length of about 5 to 10 millimeters. In some embodiments, the barrel portion 306 has a barrel length of about 5 to 15 millimeters from its first end to its second end, and a barrel diameter of about 10 to 25 millimeters. In some embodiments, the elongate members 312, 314, 316, 318, and 320 can have diameters of between about 0.008 inches (0.02032 centimeters) to 0.012 inches (0.03048 centimeters). In some embodiments, dimensions can be varied as suitable for the application.

In some embodiments, the anastomosis device 300 can include the barrel portion 306 including a rigid frame having a first end and a second end. The first flange portion 302 can include a plurality of the flange members 308 having a first length and a plurality the flange members 310 having a second length. One of the hinge members 322 can include the cover material 212 and can flexibly couple the first end of the barrel portion 306 and the first flange portion 302. The second flange portion 304 can include a plurality of the flange members 308 having a third length and a plurality of the flange members 310 having a fourth length. Another hinge member 322 can flexibly couple the second end of the barrel portion 306 and the second flange portion 304. The first length can be less than the second length. At least one of the first length and the second length can be different from at least one of the third length and the fourth length. In some embodiments, both of the first length and the second length can be different from at least one of the third length and the fourth length. In some embodiments, both of the first length and the second length can be different from both of the third length and the fourth length.

In some embodiments, the anastomosis device 300 includes the barrel portion 306 having a rigid framework and having a first end and a second end. The first flange portion 302 can include a plurality of the flange members 308 having a first projecting angle and a plurality the flange members 310 having a second projecting angle. One of the hinge members 322 can include the cover material 212 and can flexibly couple the first end of the barrel portion 306 and the first flange portion 302. The second flange portion 304 can include a plurality of the flange members 308 having the first projecting angle and a plurality the flange members 310 having the second projecting angle. Another hinge member 322 can flexibly couple the second end of the barrel portion 306 and the second flange portion 304. In some embodiments, the first projecting angle is different than the second projecting angle. In some embodiments, the first projecting angle is equal to the second projecting angle.

In some embodiments, the flange members 308 and 310 can extend from the barrel portion 306 by an angle that is less than 90 degrees in a relaxed state. In some embodiments, the flange members 308 can extend from the barrel portion 306 by an angle of between about 10 degrees and about 90 degrees in a relaxed state. In some embodiments, the flange members 310 can extend from the barrel portion 306 by an angle of between about 5 degrees and about 80 degrees in a relaxed state. In some embodiments, the flange members 308 can extend from the barrel portion 306 by an angle of about 30 degrees in a relaxed state. In some embodiments, the flange members 310 can extend from the barrel portion 306 by an angle of about 10 degrees in a relaxed state. In some embodiments, dimensions and geometries can be varied as suitable for the particular application.

In some embodiments, the covering material 212 can cover substantially all of the device 300, including all of the flange portions 302 and 304 as well as the barrel portion 306. In some embodiments, the covering material 212 can cover less than all of the device 300. In some embodiments, the covering material 212 can be formed by a single sheet of material covering the device 300. In other embodiments, the covering material 212 can be formed by multiple separate sheets of material. For example, in some embodiments the covering material 212 can include a first sheet of material covering the flange members 308 of the flange portion 302 and a second sheet of material covering the flange members 310 of the flange portion 302. In some embodiments, the second sheet of material does not cover the first flange members 308. In some embodiments, the covering material 212 can also have a third sheet of material covering the barrel portion 306, a fourth sheet of material covering the flange members 308 of the flange portion 304, and a fifth sheet of material covering the flange members 310 of the flange portion 304. This can enable a design with different covering materials 212 for each length of the flange members 308 and 310 in a given one of the flange portions 302 or 304.

Suitable materials for the elongate elements of the devices provided herein include a variety of metallic materials including alloys exhibiting, shape memory, elastic and super-elastic characteristics. Shape memory refers to the ability of a material to revert to an originally memorized shape after plastic deformation by heating above a critical temperature. Elasticity is the ability of a material to deform under load and return to its original shape when the load is released. Most metals will deform elastically up to a small amount of strain. Super-elasticity refers to the ability of a material to deform under strain to much larger degree than typical elastic alloys, without having this deformation become permanent. For example, the super-elastic materials included in the frames of some anastomosis device embodiments provided herein are able to withstand a significant amount of bending and flexing and then return to the frame's original form without deformation. In some embodiments, suitable elastic materials include various stainless steels which have been physically, chemically, and otherwise treated to produce a high springiness, metal alloys such as cobalt chrome alloys (e.g., ELGILOY™, MP35N, L605), platinum/tungsten alloys. Embodiments of shape memory and super-elastic alloys include the NiTi alloys, ternary shape memory alloys such as NiTiPt, NiTiCo, NiTiCr, or other shape memory alloys such as copper-based shape memory alloys. Additional materials could combine both shape memory and elastic alloys such as drawn filled tube where the outer layer is constructed of nitinol and the inner core is a radiopaque material such as platinum or tantalum. In this construct, the outer layer provides the super-elastic properties and the inner core remains elastic due to lower bending stresses.

In some embodiments, the elongate elements used to construct the devices provided herein can be treated in various ways to increase the radiopacity of the devices for enhanced radiographic visualization. In some embodiments, the devices are at least partially a drawn-filled type of NiTi containing a different material at the core, such as a material with enhanced radiopacity. In some embodiments, the devices include a radiopaque cladding or plating on at least portions of the first flange portion, the second flange portion, and the barrel portion. In some embodiments, one or more radiopaque markers are attached to the devices. In some embodiments, the elongate elements and/or other portions of the devices provided herein are also visible via ultrasound.

In some embodiments, the first flange portion 302, the second flange portion 304, and the barrel portion 306, can comprise a framework of interconnected elongate elements that is constructed by cutting a tube. In one such embodiment, a tube of metallic material (e.g., nitinol, stainless steel, cobalt, etc.) can be laser cut, and then the tube is expanded and shaped into the desired configuration. In some such embodiments, the metallic material is heat-set in the desired configuration so that the material receives a shape-memory whereby the material will naturally strive to attain the desired configuration. In some embodiments, shape memory materials such as nitinol may strive to attain the desired configuration when exposed to body temperature.

As described further below, a covering material 212 can be disposed on some portions or on all of the first flange portion 302, the second flange portion 304, and/or the barrel portion 306. In some embodiments, portions of the first flange portion 302, the second flange portion 304, and/or the barrel portion 306 can remain free of the covering material 212.

In some embodiments, the materials and configuration of the anastomosis device 300 (and the other anastomosis device embodiments provided herein) allow the devices to be elastically crushed, folded, and/or collapsed into a low-profile delivery configuration for containment within a lumen for transcatheter or endoscopic/thoracoscopic delivery, and to self-expand to an operative size and configuration once positioned at a desired target site within a body and deployed from the lumen. For example, the anastomosis device 300 can be configured in a collapsed delivery configuration in which the plurality of struts 308 are radially compressed such that they are forced to extend substantially parallel to the axis of the barrel portion 306, and in which the diameter of the barrel portion 306 is also crushed to become smaller. Due to the use of such materials and structure, the device 300 may also exhibit, for example, beneficial fatigue resistance and elastic properties.

After deployment, the plurality of struts 308 extend from the barrel portion 306 at a radial orientation and geometry to exert a desired level of apposition pressure on the tissue. In some embodiments, the plurality of struts 308 extend from the barrel portion 306 such that the nominal measure of the angle between the struts 308 and the longitudinal axis of the device 300 is about 100°, or about 90°, or about 80°, or about 70°, or about 60°, or about 50°, or about 40°, or about 30°, or about 20°, or about 10°, and the like. In some embodiments, the plurality of struts 308 extend from the barrel portion 306 such that the nominal measure of the angle between the struts 308 and the longitudinal axis of the device 300 is in a range from about 80° to about 100°, or about 70° to about 90°, or about 60° to about 80°, or about 50° to about 70°, or about 40° to about 60°, or about 30° to about 50°, or about 20° to about 40°, or about 10° to about 30°.

The flange member 308 and 310 can comprise a variety of materials including, but not limited to, metallic shape memory materials and super-elastic alloys. Thus, the flange member 308 and 310 can be configured to self-expand to an expanded deployed configuration, e.g., including to a predetermined angle.

The barrel portion 306 is shown in a deployed or expanded configuration. In some embodiments, the barrel portion 306, as described above, can comprise a variety of metallic shape memory materials and super-elastic alloys. Thus, the barrel portion 306 can be configured to self-expand to the deployed configuration. In some embodiments, the barrel portion 306 is balloon expandable to the deployed configuration, or supplemental expansion forces can be applied to a self-expandable device by balloon dilation. The diameter of the barrel portion 306 can be made in any size as desired in order to suit the intended use and/or delivery system of the anastomosis device 300. For example, in the low-profile delivery configuration the anastomosis device 300 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. When the anastomosis device 300 is configured in its expanded deployed configuration as shown, the diameter of the barrel portion 306 increases to a deployed diameter. In some implementations, the deployed outer diameter of the barrel portion 306 is configured to at least partially anchor the device 300 via an interference fit with the tissue aperture in which the barrel portion 306 resides. However, in some implementations the deployed outer diameter of the barrel portion 306 is slightly less than the diameter of the tissue aperture in which the barrel portion 306 resides, and the flange portions 302 and 304 compress the tissue to provide the migration resistance. In some embodiments, the fully expanded diameter of the barrel portion 306 is about 30 mm, or about 25 mm, or about 20 mm, or about 15 mm, or about 12 mm, or about 10 mm, or about 8 mm, or about 6 mm, or about 4 mm, and the like. In some embodiments, the fully expanded diameter of the barrel portion 306 is in a range between about 20 mm to about 30 mm, or about 15 mm to about 25 mm, or about 10 mm to about 20 mm, or about 5 mm to about 15 mm, or about 4 mm to about 8 mm, and the like.

The anastomosis device 300 also includes the covering material 212. In some embodiments, the covering material 212 is disposed on at least some portions (or on all) of the first flange portion 302, the second flange portion 304, and the barrel portion 306. In some embodiments, some portions of the first flange portion 302, the second flange portion 304, and/or the barrel portion 306 are not covered by the covering material 212.

In some embodiments, the covering material 212 is generally fluid impermeable. That is, in some embodiments the covering material 212 may be made of a material that inhibits or reduces passage of blood, bile and/or other bodily fluids and materials through the covering material 212 itself. In some embodiments, the covering material 212 has a material composition and configuration that inhibits or prevents tissue ingrowth and/or endothelialization or epithelialization into the covering material 212. Some such embodiments that are configured to inhibit or prevent tissue ingrowth and/or endothelialization can be more readily removed from the patient at a future date if so desired. In some embodiments, the covering material 212, or portions thereof, has a microporous structure that provides a tissue ingrowth scaffold for durable sealing and/or supplemental anchoring strength of the anastomosis device 300.

In some embodiments, the covering material 212 comprises a fluoropolymer, such as an expanded polytetrafluoroethylene (ePTFE) polymer or polyvinylidene difluoride (PVDF) polymer. In some embodiments, the covering material 212 comprises a polyester, a silicone, a urethane, another biocompatible polymer, polyethylene terephthalate (e.g., Dacron®), bioabsorbable materials, copolymers, or combinations and subcombinations thereof. In some embodiments, the covering material 212 comprises a bioabsorbable web. In some embodiments, the bioabsorbable material can also provide an anti-migration feature by promoting attachment between the device 300 and tissue until the bioabsorbable material is absorbed.

In some embodiments, the covering material 212 (or portions thereof) is modified by one or more chemical or physical processes that enhance one or more properties of the material 212. For example, in some embodiments, a hydrophilic coating may be applied to the covering material 212 to improve the wettability and echo translucency of the material 212. In some embodiments, the covering material 212, or portions thereof, may be modified with chemical moieties that facilitate one or more of endothelial cell attachment, endothelial cell migration, endothelial cell proliferation, and resistance to or promotion of thrombosis. In some embodiments, the covering material 212, or portions thereof, may be modified to resist biofouling. In some embodiments, the covering material 212, or portions thereof, may be modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments, the drug substance is a corticosteroid, a human growth factor, an anti-mitotic agent, an antithrombotic agent, a stem cell material, or dexamethasone sodium phosphate, to name some embodiments. In some embodiments, a pharmacological agent may be delivered separately from the covering material 212 to the target site to promote tissue healing or tissue growth.

Coatings and treatments may be applied to the covering material 212 before or after the covering material 212 is joined or disposed on the framework of the anastomosis device 300. Additionally, one or both sides of the covering material 212, or portions thereof, may be coated. In some embodiments, certain coatings and/or treatments are applied to the covering material(s) 212 located on some portions of the anastomosis device 300, and other coatings and/or treatments are applied to the material(s) 212 located on other portions of the anastomosis device 300. In some embodiments, a combination of multiple coatings and/or treatments are applied to the covering material 212, or portions thereof. In some embodiments, certain portions of the covering material 212 are left uncoated and/or untreated. In some embodiments, the device 300 is fully or partially coated to facilitate or frustrate a biological reaction, such as, but not limited to, endothelial cell attachment, endothelial cell migration, endothelial cell proliferation, and resistance to or promotion of thrombosis.

In some embodiments, a first portion of the covering material 212 is formed of a first material and a second portion of the covering material 212 is formed of a second material that is different than the first material. In some embodiments, the covering material 212 is comprised of multiple layers of materials, which may be the same or different materials. In some embodiments, portions of the covering material 212 have one or more radiopaque markers attached thereto to enhance in vivo radiographic visualization of the anastomosis device 300, or one or more echogenic areas to enhance ultrasonic visibility.

In some embodiments, one or more portions of the covering material 212 are attached to the framework of the device 300, such as the barrel portion 306 and/or the flange portions 302 and 304. The attachment can be accomplished by a variety of techniques such as, but not limited to, stitching the covering material 212 to the framework of the device 300, adhering the covering material 212 to the framework of the device 300, laminating multiple layers of the covering material 212 to encompass portions of the elongate members of the device 300, using clips or barbs, laminating multiple layers of the covering material together through openings in the framework of the device 300. In some embodiments, the covering material 212 is attached to the framework of the device 300 at a series of discrete locations thereby facilitating the flexibility of the framework. In some embodiments, the covering material 212 is attached to the framework of the device 300 loosely. In some embodiments, the covering material 212 is attached to the framework using other such techniques or combinations of such techniques.

In some embodiments, the framework of the device 300 (or portions thereof) is coated with a bonding agent (e.g., fluorinated ethylene propylene (FEP) or other suitable adhesive) to facilitate attachment of the covering material 212 to the framework. Such adhesives may be applied to the framework using contact coating, powder coating, dip coating, spray coating, or any other appropriate means.

Figure 3:
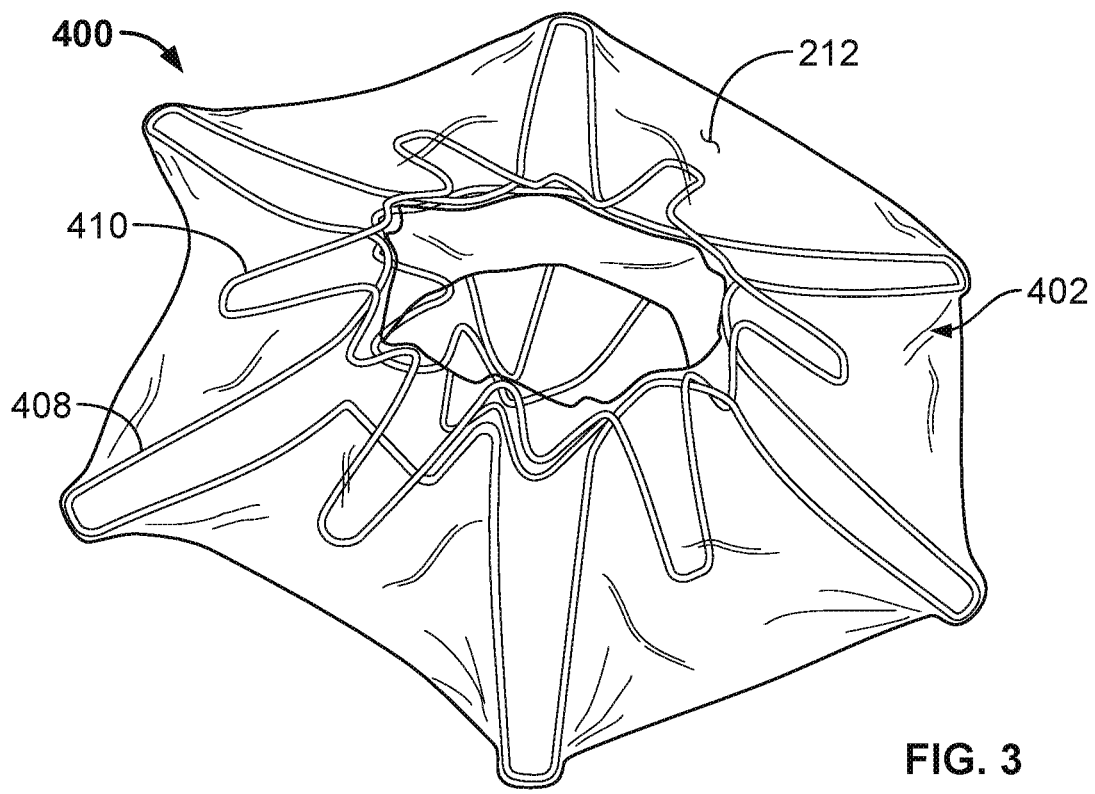
FIG. 3 is a perspective view of another exemplary anastomosis device in accordance with some embodiments.
Figure 4A:
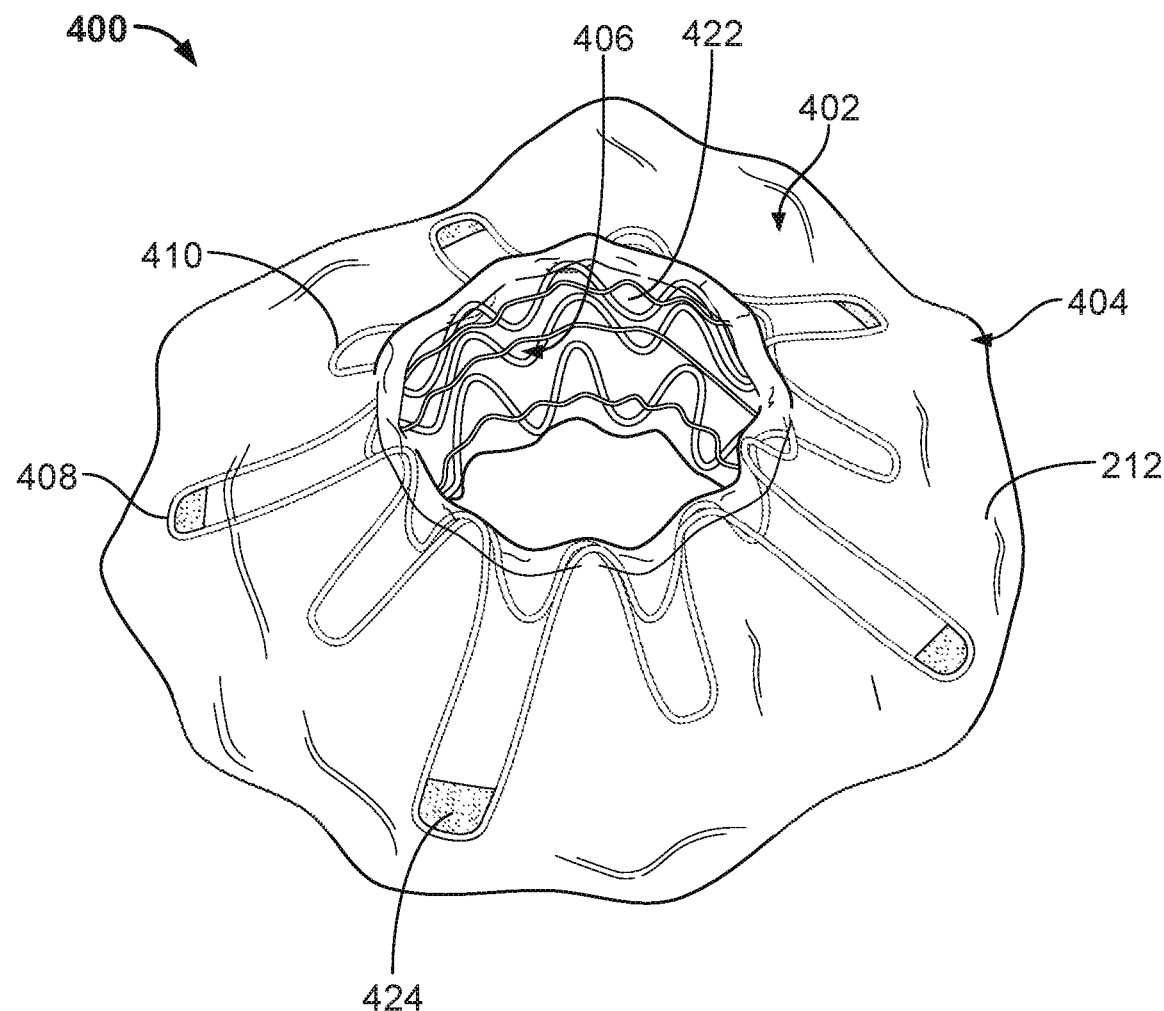
FIG. 4A is a perspective view of another exemplary anastomosis device in accordance with some embodiments.

FIGS. 3 and 4A are perspective views of another exemplary anastomosis device 400 in accordance with some embodiments. The anastomosis device 400 is shown having a first flange portion 402, a second flange portion 404, a barrel portion 406, and covering material 212. The first flange portion 402 and the second flange portion 404 (also referred to herein as flange portions, flanges, etc.) can each include one or more flange members 408 and 410 (also referred to herein as anchor members, apposition members, fins, etc.). The flange members 408 and 410 can have different configurations (e.g., lengths, widths, shapes, angles, etc.). The covering material 212 can form hinge members 422, allowing the flange members 408 and 410 to pivot with respect to the barrel portion 406. In some embodiments, the anastomosis device 400 can have features and functionality similar to that described with respect to anastomosis device 300 and other anastomosis devices described herein.

In some embodiments, such as shown in FIG. 4A, one or more of the flange members 408 can include radiopaque markers 424 at distal regions thereof. In some embodiments, the anastomosis device 400 can include radiopaque markers 424 on some but not all flange members of the anastomosis device. For example, in the illustrated embodiment, the anastomosis device 400 includes radiopaque markers 424 at distal regions of the flange members 408 but not at the distal ends of any of the flange members 406. In some embodiments, the position of the radiopaque markers 424 can be varied as suitable for the application.

Figure 4B:
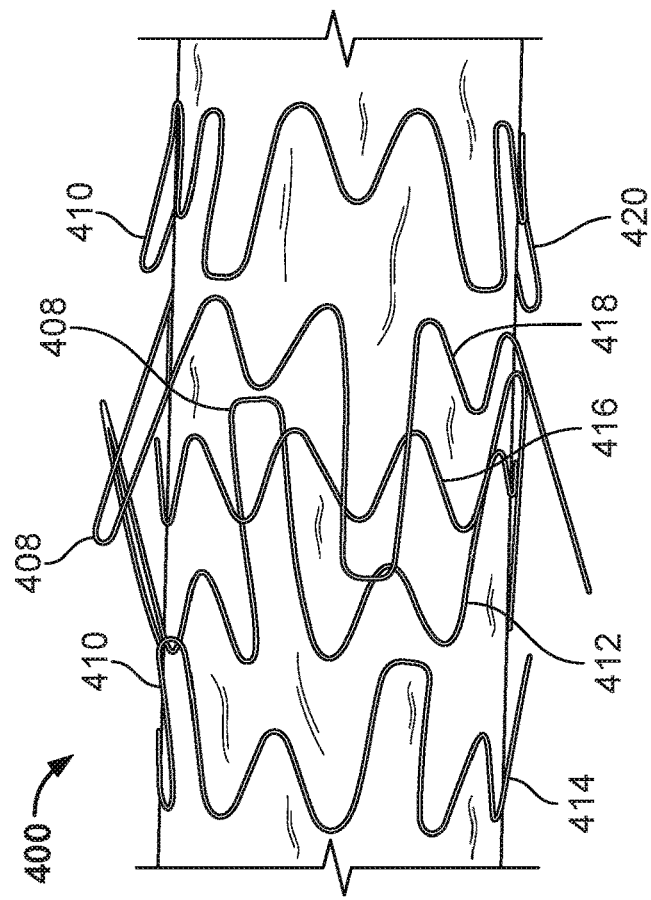
FIG. 4B is an exploded view of the anastomosis device of FIG. 4A.

FIG. 4B is an exploded view of the anastomosis device 400 with the covering material 212 removed. The anastomosis device can include elongate members 412, 414, 416, 418, and 420. In the illustrated embodiment, the anastomosis device 400 includes five separate elongate members. The elongate member 412 defines the flange members 408 of the first flange portion 402. The elongate member 414 defines the flange members 410 of the first flange portion 402. The elongate member 416 defines a rigid frame of the barrel portion 406. The elongate member 418 defines the flange members 408 of the second flange portion 404. The elongate member 420 defines the flange members 410 of the second flange portion 404. Two elongate members 412 and 414 support the first flange portion 402, two elongate members 418 and 420 support the second flange portion 404, and one elongate member 416 supports the barrel portion 406. Thus, the separate elongate members 412, 414, 416, 418, and 420 can combine with the covering material 212 to form the anastomosis device 400. The elongate members 412, 414, 416, 418, and 420 can combine such that the flange members 408 alternate with the flange members 410. Hinges for the flange members 408 can align with the flange members 410 and hinges for the flange members 410 can align with the flange members 408. Accordingly, each of the flange members 408 and 410 can hinge separately.

Figure 5:
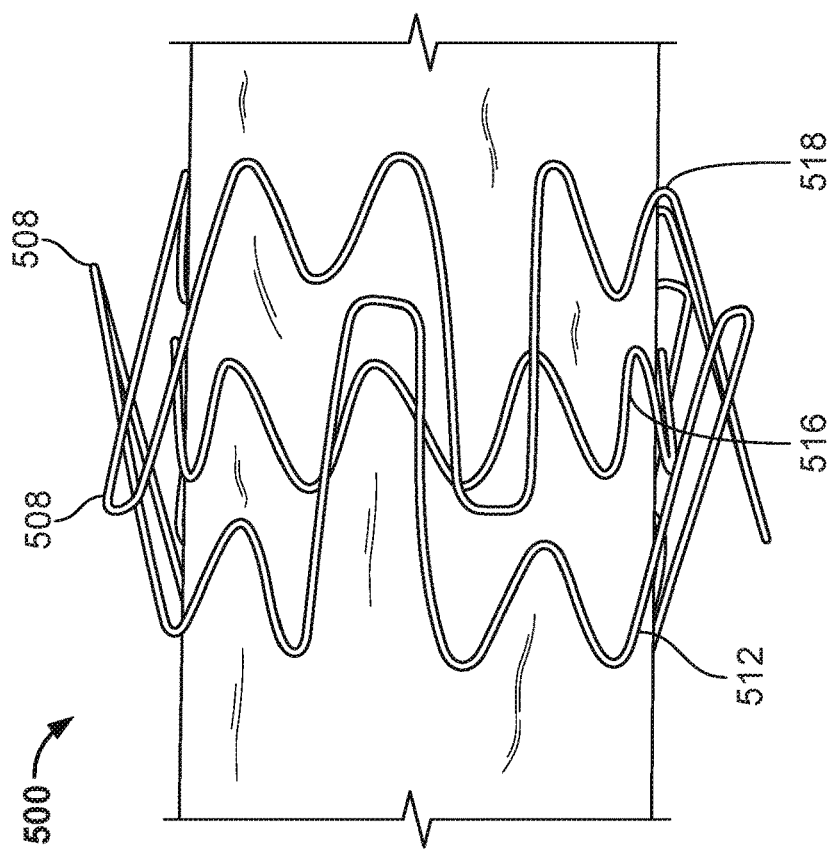
FIG. 5 is an exploded view of another exemplary anastomosis device in accordance with some embodiments.

FIG. 5 is an exploded view of another exemplary anastomosis device 500 in accordance with some embodiments. The anastomosis device 500 can include flange members 508 and elongate members 512, 516, and 518. In the illustrated embodiment, the anastomosis device 500 includes three separate elongate members. The elongate member 512 defines the flange members 508 of a first flange portion. The elongate member 516 defines a rigid frame of a barrel portion. The elongate member 518 defines the flange members 508 of a second flange portion. In the anastomosis device 500, one elongate member 512 supports the first flange portion, one elongate member 518 supports the second flange portion, and one elongate member 516 support the barrel portion. Thus, the separate elongate members 512, 516, and 518 can combine with the covering material 212 (not shown in FIG. 5) to form the anastomosis device 500. The anastomosis device 500 has features and functionality similar or identical to that described with respect to anastomosis device 300.

FIG. 6 is a perspective view of another exemplary anastomosis device 600 in accordance with some embodiments. The anastomosis device 600 is shown having a first flange portion 602, a second flange portion 604, a barrel portion 606, and covering material 212. The first flange portion 602 and the second flange portion can each include one or more flange members 608 and 610. The flange members 608 and 610 can have different configurations (e.g., lengths, widths, shapes, angles, etc.). The covering material 212 can form the hinge members 622, allowing the flange members 608 and 610 to pivot with respect to the barrel portion 606. In some embodiments, the covering 212 need not cover all of the flange members 708. The anastomosis device 600 has features and functionality similar or identical to that described with respect to anastomosis device 300.

FIG. 7 is a perspective view of another exemplary anastomosis device in accordance with some embodiments. The anastomosis device 700 is shown having a first flange portion 702, a second flange portion 704, a barrel portion 706, and covering material 212. The first flange portion 702 and the second flange portion can each include one or more flange members 708. The flange members 708 can have different configurations (e.g., lengths, widths, shapes, angles, etc.). The covering material 212 can form the hinge members 722, allowing the flange members 708 to pivot with respect to the barrel portion 706. In some embodiments, the covering 212 need not cover all of the flange members 708. In some embodiments, the anastomosis device 700 can include flange members 708 having a substantially common length around each respective flange portion 702 and 704, as opposed to alternating long and short flange members 708. In some of such embodiments, angle of the flange members 708 can be varied. In some embodiments, length of the flange members 708 can be varied. For example, length of the flange members 708 can be varied symmetric or asymmetrically. The anastomosis device 700 has features and functionality similar or identical to that described with respect to anastomosis device 300.

FIG. 8 is a perspective view of another exemplary anastomosis device in accordance with some embodiments. The anastomosis device 800 is shown having a first flange portion 802, a second flange portion 804, a barrel portion 806, and covering material 212. The first flange portion 802 and the second flange portion can each include one or more flange members 808. The flange members 808 can have different configurations (e.g., lengths, widths, shapes, angles, etc.). The covering material 212 can form the hinge members 822, allowing the flange members 808 to pivot with respect to the barrel portion 806. In some embodiments, the anastomosis device 800 can include flange members 808 having a substantially common length around each respective flange portion 802 and 804, as opposed to alternating long and short flange members 808. In some of such embodiments, angle of the flange members 808 can be varied. In some embodiments, length of the flange members 808 can be varied in a manner similar to embodiments discussed above. For example, length of the flange members 808 can be varied symmetric or asymmetrically. The anastomosis device 800 has features and functionality similar or identical to that described with respect to anastomosis device 300.

FIG. 9 is a perspective view of another exemplary anastomosis device in accordance with some embodiments. The anastomosis device 900 is shown having a first flange portion 902, a second flange portion 904, a barrel portion 906, and covering material 212. The first flange portion 902 and the second flange portion can each include one or more flange members 908. The flange members 908 can have different configurations (e.g., lengths, widths, shapes, angles, etc.). In some embodiments, the covering 212 need not cover all of the flange members 908. In some embodiments, the anastomosis device 900 can include one or more additional reinforcement elongate members 924 to reduce or prevent buckling at a connection point between the flange members 908 and the barrel portion 906. The reinforcement elongate members 924 can reduce or prevent pivoting action by the flange members 908 and reinforce the barrel portion 906 as well as the flange portions 902 and 904. The reinforcement elongate members 924 can reduce or prevent narrowing of the anastomosis device 900 post implantation. Apposition forces can be higher than in embodiments with hinge portions due to connection of the flange members 908 to the reinforcement elongate members 924 at proximal ends of the flange members 908. The anastomosis device 900 can have features and functionality similar or identical to that described with respect to anastomosis device 300.

FIG. 10 is a perspective view of another exemplary anastomosis device in accordance with some embodiments. The anastomosis device 1000 is shown having a first flange portion 1002, a second flange portion 1004, a barrel portion 1006, and covering material 212. The first flange portion 1002 and the second flange portion can each include one or more flange members 1008. The flange members 1008 can have different configurations (e.g., lengths, widths, shapes, angles, etc.). In some embodiments, the anastomosis device 1000 can include one or more additional reinforcement elongate members 1024 positioned at or proximate a rim of the barrel portion 1006. The reinforcement elongate members 1024 can reduce or prevent pivoting action by the flange members 1008 and reinforce the barrel portion 1006 as well as the flange portions 1002 and 1004. The reinforcement elongate members 1024 can provide a straighter edge for the anastomosis device 1000 and can reduce or prevent narrowing of the anastomosis device 1000 post implantation. Apposition forces can be higher than in embodiments with hinge portions. In some embodiments, the covering 212 need not cover all of the flange members 1008. The anastomosis device 1000 has features and functionality similar or identical to that described with respect to anastomosis device 300.

FIG. 11 is a perspective view of another exemplary anastomosis device in accordance with some embodiments. The anastomosis device 1100 is shown having a first flange portion 1102, a second flange portion 1104, a barrel portion 1106, and covering material 212. The first flange portion 1102 and the second flange portion can each include one or more flange members 1108. The flange members 1108 can have different configurations (e.g., lengths, widths, shapes, angles, etc.). In some embodiments, the covering 212 need not cover all of the flange members 1108. The flange members 1108 can connect directly to one or more elongate members 1116 that form a rigid frame for the barrel portion 1106. This connection can reduce or prevent buckling at a connection point between the flange members 1108 and the barrel portion 1106. This connection can reduce or prevent pivoting action by the flange members 1108 and reinforce the barrel portion 1106 as well as the flange portions 1102 and 1104. This connection can reduce or prevent narrowing of the anastomosis device 1100 post implantation. Apposition forces can be higher than in embodiments with hinge portions due to connection of the flange members 1108 to the elongate members 1116 at proximal ends of the flange members 1108. The anastomosis device 1100 has features and functionality similar or identical to that described with respect to anastomosis device 300.

FIG. 12 is a side view of another exemplary anastomosis device 1200 in accordance with some embodiments. The anastomosis device 1200 is shown having a first flange portion 1202, a barrel portion 1206, and covering material 212. The first flange portion 1202 includes flange members 1208 and 1210. The flange members 1208 and 1210 can have different configurations (e.g., lengths, widths, shapes, angles, etc.). In FIG. 12, the anastomosis device is shown deployed and expanded, as if in an operative site of a patient. Consequently, the second flange portion (not shown) is obscured in FIG. 12. The covering material 212 can form the hinge members 1222, which can allow the flange members 1208 and 1210 to pivot with respect to the barrel portion 1206 to the deployed position shown in FIG. 12. The anastomosis device 1200 has features and functionality similar or identical to that described with respect to anastomosis device 300.

In some embodiments, the devices provided herein can be used for sealing or anchoring a heart valve implant. A heart valve implant enables one-way flow of blood from a heart chamber and usually has a first inflow end and a second outflow end. The contractions of the heart cause flow of blood through the valve from the inflow end to the outflow end. Between the inflow and outflow ends, a valve assembly within the heart valve implant provides for one way flow, opening to allow flow from the inflow to the outflow end when the pressure of the blood is higher on the inflow end, and closing to prevent flow when the pressure on the outflow end is higher than the inflow end. In some embodiments, the device includes a tunnel or central aperture through the device with apposition portions to anchor a valve assembly and seal against backward flow. A valve assembly can be attached in the tunnel or central aperture. The apposition portions of the device can be configured to be highly conformable to the topography of the heart chambers or blood vessels, and compliant with the beating movements of the heart. In some embodiments, a covering material is configured to allow flow through a valve assembly in the tunnel or aperture while preventing flow around the apposition portions.

It should be understood that one or more design features of the anastomosis devices provided herein can be combined with other features of other anastomosis devices provided herein. In effect, hybrid designs that combine various features from two or more of the anastomosis device designs provided herein can be created, and are within the scope of this disclosure.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device comprising:
a plurality of struts forming:
  a barrel portion having a first end and a second end defining a first length between the first end and the second end, the first length having a midway point positioned centrally between the first end and the second end, and a tunnel or central aperture therethrough,
  a first flange portion extending from the first end of the barrel portion, the first flange portion including a plurality of first flange members that extend from the barrel portion at an angle less than 90 degrees in a relaxed state so that at least one flange member of the plurality of first flange members crosses the midway point in the relaxed state, the plurality of first flange members being configured to apply an apposition force against a first tissue side,
  a second flange portion extending from the second end of the barrel portion, the second flange portion including a plurality of second flange members that extend from the barrel portion at an angle less than 90 degrees in a relaxed state and are configured to apply an apposition force against a second tissue side, and the first flange portion and the second flange portion are configured to move independently of each other, wherein at least one flange member of the plurality of second flange members crosses the at least one flange member of the plurality of first flange members; and
  a valve assembly arranged within the barrel portion and configured to allow blood flow through the tunnel or central aperture.

2. The implantable medical device of claim 1, wherein the first flange portion and the second flange portion are configured to anchor the valve assembly and seal against backward flow.

3. The implantable medical device of claim 2, wherein the first flange portion is configured to apply a first apposition force against the first tissue side and the second flange portion is configured to apply a second apposition force against the second tissue side to conform to tissue topography.

4. The implantable medical device of claim 3, wherein the first flange portion and the second flange portion are configured to conform to the tissue topography of heart chambers or blood vessels.

5. The implantable medical device of claim 3, wherein the first apposition force is different from the second apposition force.

6. The implantable medical device of claim 1, further including a covering coupled to at least one of the first flange portion, the second flange portion, and the barrel portion so that the covering extends along a length of the barrel portion between the first flange portion and the second flange portion, and the covering is configured to allow flow through the valve assembly in the tunnel or aperture while preventing flow around the first flange portion and the second flange portion.

7. The implantable medical device of claim 6, wherein the covering is configured to inhibit or prevent tissue ingrowth into at least a portion of the covering material.

8. The implantable medical device of claim 6, wherein the covering is configured to promote tissue ingrowth into at least a portion of the covering material.

9. The implantable medical device of claim 1, wherein the first flange portion and the second flange portion are configured to move independently of each other to facilitate conformability with tissue topography.

10. The implantable medical device of claim 1, wherein an outer diameter of the barrel portion is configured to at least partially anchor via an interference fit with a tissue aperture in which the barrel portion resides.

11. The implantable medical device of claim 1, wherein the first flange portion and the second flange portion are configured to fold parallel to the tunnel or central aperture in a delivery configuration.

12. An implantable medical device comprising:
a valve assembly configured to allow blood flow through a central aperture, the valve assembly defining a first length having a central midway point;
a first flange portion including a plurality of first flange members that extend from the valve assembly at an angle less than 90 degrees in a relaxed state so that at least one flange member of the plurality of first flange members crosses the central midway point, and the plurality of first flange members are configured to apply an apposition force against a first tissue side; and
a second flange portion including a plurality of second flange members that extend from the valve assembly at an angle less than 90 degrees in a relaxed state and are configured to apply an apposition force against a second tissue side, the valve assembly positioned between the first flange portion and the second flange portion, wherein at least one flange member of the plurality of second flange members crosses the at least one flange member of the plurality of first flange members;

wherein the first flange portion and the second flange portion are configured to move independently of each other and anchor the valve assembly and seal against backward flow.

13. The implantable medical device of claim 12, wherein the first flange portion and the second flange portion are configured to collapse to a low-profile delivery configuration and extend substantially parallel to a longitudinal axis of the central aperture.

14. The implantable medical device of claim 13, wherein the first flange portion and the second flange portion are configured to self-expand upon positioning at a target site.

15. The implantable medical device of claim 13, wherein the first flange portion extends from a first end of a barrel portion and the second flange portion extends from a second end of the barrel portion.

16. The implantable medical device of claim 15, wherein the first flange portion and the second flange portion are configured to extend from the barrel portion at a radial orientation and geometry to exert an apposition pressure on tissue in response to self-expanding at a desired target site.

17. The implantable medical device of claim 12, wherein the first flange portion and the second flange portion are configured to conform to the tissue topography of heart chambers or blood vessels.

18. The implantable medical device of claim 12, further comprising a covering extending along a length defined between the first flange portion and the second flange portion.

* * * * *